United States Patent
Liu et al.

(10) Patent No.: US 11,732,279 B2
(45) Date of Patent: Aug. 22, 2023

(54) METHOD AMD STRAINS FOR REDUCING BYPRODUCT FUMARIC ACID IN FERMENTATION PROCESS OF L-MALIC ACID AND USE THEREOF

(71) Applicant: Nanjing Haohe Biotechnology Co., Ltd., Nanjing (CN)

(72) Inventors: Hao Liu, Nanjing (CN); Qing Xu, Nanjing (CN)

( * ) Notice: Subject to any disclaimer, the term of this patent is extended or adjusted under 35 U.S.C. 154(b) by 0 days.

(21) Appl. No.: 17/744,782

(22) Filed: May 16, 2022

(65) Prior Publication Data
US 2023/0167471 A1    Jun. 1, 2023

(30) Foreign Application Priority Data

Dec. 1, 2021    (CN) .......................... 202111445683.8

(51) Int. Cl.
| | | |
|---|---|---|
| *C12P 7/46* | (2006.01) | |
| *C12N 1/14* | (2006.01) | |
| *C12N 15/80* | (2006.01) | |
| *C12R 1/685* | (2006.01) | |

(52) U.S. Cl.
CPC .............. *C12P 7/46* (2013.01); *C12N 1/145* (2021.05); *C12N 15/80* (2013.01); *C12N 2800/10* (2013.01); *C12R 2001/685* (2021.05)

(58) Field of Classification Search
None
See application file for complete search history.

(56) References Cited

U.S. PATENT DOCUMENTS

| | | | | |
|---|---|---|---|---|
| 2004/0038392 A1* | 2/2004 | Shibui | .................... | C12N 15/85 435/320.1 |
| 2010/0009419 A1* | 1/2010 | Burk | ........................ | C12N 9/88 435/254.22 |
| 2014/0186910 A1* | 7/2014 | Maggio-Hall | ............ | C12P 7/40 435/252.32 |
| 2018/0371468 A1* | 12/2018 | Mojzita | ................ | C12N 15/625 |

FOREIGN PATENT DOCUMENTS

| | | |
|---|---|---|
| CN | 1523115 A | 8/2004 |
| CN | 101255405 A | 9/2008 |
| CN | 104046577 A | 9/2014 |
| CN | 110734865 A | 1/2020 |
| CN | 111218408 A | 6/2020 |
| WO | 2010111344 A2 | 9/2010 |

OTHER PUBLICATIONS

Accession A0A254U8U7. Nov. 22, 2017 (Year: 2017).*
Accession AM270282. Mar. 14, 2015. Alignment to SEQ ID No. 3 (Year: 2015).*
Accession AM270282. Mar. 14, 2015. Alignment to SEQ ID No. 4 (Year: 2015).*
Xu et al. ACS Synth Biol. Jun. 19, 2020;9(6):1418-1425. Epub May 7, 2020 (Year: 2020).*

* cited by examiner

*Primary Examiner* — Christian L Fronda

(57) ABSTRACT

The disclosure discloses an *Aspergillus niger* engineered strain for reducing byproduct fumaric acid in a fermentation process of L-malic acid. The *Aspergillus niger* engineered strain is an *Aspergillus niger* engineered strain in which a fumarate hydratase gene fum is knocked out. The disclosure overcomes the defects in the prior art, in the current process of producing malic acid through fermentation of *Aspergillus niger*, byproduct fumaric acid can be accumulated with the generation of malic acid so as to cause the improved cost of the subsequent malic acid purification process. The disclosure provides an *Aspergillus niger* engineered strain in which a fum gene is knocked out and a method for greatly reducing byproduct fumaric acid in the fermentation production of *Aspergillus niger*.

1 Claim, 7 Drawing Sheets
Specification includes a Sequence Listing.

METHOD AMD STRAINS FOR REDUCING BYPRODUCT FUMARIC ACID IN FERMENTATION PROCESS OF L-MALIC ACID AND USE THEREOF

CROSS REFERENCE TO RELATED APPLICATIONS

This application claims foreign priority of Chinese Patent Application No. 202111445683.8, filed on Dec. 1, 2021 in the China National Intellectual Property Administration, the disclosures of all of which are hereby incorporated by reference.

TECHNICAL FIELD

The disclosure belongs to the technical field of biological engineering, particularly to a method and strains for reducing byproduct fumaric acid in a fermentation process of L-malic acid, and use thereof.

BACKGROUND OF THE PRESENT INVENTION

L-malic acid, as an important organic acid, is widely present in plants, animals and microorganisms, is an important intermediate mesostate in a tricarboxylic acid cycle in an organism and widely applied to the fields of foods, medicines and chemical industry and the like. In food industry, malic acid combined with citric acid is broadly used as a food sour regulating agent due to natural fragrance of apples. In addition, malic acid can be used for food preservation and is combined with other preservatives, etc.; in medicine industry, malic acid is often used for treating abnormal liver functions and hyperammonemia because it can directly participate in metabolism of a human body, and is also often used in amino acid injection drugs to help the utilization of amino acids, etc.; in chemical industry, malic acid is ordinarily used for metal cleaning, printing and dyeing industry, non-electrolysis cladding layers, oil varnish and the like. Malic acid is initially extracted from fruits such as apples, and this method cannot satisfy the demand of a large-scale market due to limitation by contents, raw materials and other factors.

At present, industrialized production ways of malic acid mainly include a chemical synthesis method and a biological catalysis method. The chemical synthesis method uses petroleum base chemical benzene as a raw material to obtain racemic DL-malic acid under the conditions of high temperature and high pressure; as early as 1970, FDA banned DL-malic acid to be added in infant foods; in addition, the chemical synthesis method has high equipment requirements and fast equipment depreciation, which restricts its application in the fields of foods and medicines. Moreover, raw material sources of this method are petroleum base chemicals, which is a great challenge for increasingly decreasing petroleum energy and environment problems. The biological catalysis method is mainly an immobilized enzyme or immobilized cell transformation method. The immobilized enzyme method is high in extraction, purification and immobilization costs of an enzyme, and therefore causes revenues to be limited to a certain extent; the immobilized cell transformation method has the disadvantages that since living cells themselves contain a complicated enzyme system, many byproducts are easily formed, so as to increase the downstream purification cost of a product. In summary, malic acid prepared by the chemical synthesis method and the biological catalysis method difficultly satisfies an increasing demand on malic acid in the market.

Compared with the above two methods, a microbiological fermentation method pays more and more attentions because of its environmental friendliness, renewable carbon sources and the like. However, currently, this method has the defects of few safe strain selectivity, low product conversion rate or production efficiency, many heteroacid byproducts and high heteroacid byproduct content, which seriously restricts the industrialization progress for production of L-malic acid via a fermentation method.

By retrieval, patent public documents associated with this invention patent application have not yet been found so far.

SUMMARY OF PRESENT INVENTION

The objective of the disclosure is to provide a method and strains for reducing byproduct fumaric acid in a fermentation process of L-malic acid and use thereof, in order to overcome the problems existing in the prior art.

The technical solution adopted by the disclosure to solve the technical problem is as follows:

provided is an *Aspergillus niger* engineered strain for reducing byproduct fumaric acid in a fermentation process of L-malic acid, wherein the *Aspergillus niger* engineered strain is an *Aspergillus niger* engineered strain in which a fumarate hydratase gene fum is knocked out.

Further, the gene sequence of the fumarate hydratase gene fum is SEQ NO:1, and the amino acid sequence of the fumarate hydratase gene fum is SEQ NO:2.

Further, the fumarate hydratase gene fum is NCBI-locus-_tagANI_1_952104.

Provided is a method for constructing the *Aspergillus niger* engineered strain for reducing byproduct fumaric acid in a fermentation process of L-malic acid as described above, comprising the following steps:

(1) construction of a fumarate hydratase gene fum knockout vector respectively amplifying upstream and downstream sequence fragments of a gene fum through PCR reaction with a wild type *Aspergillus niger* ATCC1015 genome as a template, and recovering PCR products to respectively obtain target fragments; and cloning the upstream and downstream sequence fragments of the gene fum onto a vector pLH594, so as to construct a fumarate hydratase gene fum knockout vector pLH804;

wherein the upstream sequence of the gene fum is SEQ NO:3, and the downstream sequence of the gene fum is SEQ NO: 4;

(2) obtaining of an *Aspergillus niger* fumarate hydratase gene fum knockout strain:

transferring the vector pLH804 into *Aspergillus niger* malic acid high-yield strain S1149, and conducting transformant screening and hygromycin resistance gene recombination to obtain an *Aspergillus niger* fumarate hydratase gene fum knockout strain M1.

Provided is a method for fermenting L-malic acid by utilizing the *Aspergillus niger* engineered strain as described above, comprising the following steps:

inoculating the *Aspergillus niger* engineered strain into a PDA culture medium to be cultured for 5 days at 28° C. until conidia are generated, collecting the conidia and inoculating a conidium suspension into a fermentation culture medium, wherein the concentration of the conidia is $1*10^8$ conidia/50 ml, and then culturing for 5 days at a constant temperature of 28° C. at 200 rpm to obtain L-malic acid.

Further, the components and a formulation method of the fermentation culture medium are as follows:

100 g/L of glucose, 6 g/L of bacterial peptone, 0.15 g/L of anhydrous potassium dihydrogen phosphate, 0.15 g/L of anhydrous dipotassium hydrogen phosphate, 0.1 g/L of calcium chloride dihydrate, 0.1 g/L of magnesium sulfate heptahydrate, 0.005 g/L of sodium chloride, 0.005 g/L of ferrous sulfate heptahydrate and 0.001 g/L of anhydrous citric acid, a solvent is water, and autoclaving is performed for 20 min at 115° C.

Further, the yield of the L-malic acid obtained by the method is 93.56-98.16 g/L which is improved by 1.97% compared with a starting strain, and the content of the fumaric acid is 0.07-0.14 g/L which is reduced by 93.9% compared with the starting strain.

Provided is use of the *Aspergillus niger* engineered strain as described above in production of L-malic acid.

The disclosure has the beneficial effects:

1. The disclosure overcomes the defects in the prior art, in the current production process of malic acid through fermentation of *Aspergillus niger*, the byproduct fumaric acid is accumulated with the generation of malic acid so as to cause the improved cost of the subsequent malic acid purification process, and the disclosure provides an *Aspergillus niger* strain in which the fum gene is knocked out and a method for greatly reducing byproduct fumaric acid in a fermentation process of *Aspergillus niger*. By the disclosure, the byproduct fumaric acid accumulated in the process of producing L-malic acid through fermentation of *Aspergillus niger* is greatly reduced, the cost in the process of downstream separation and purification of malic acid is decreased, and good strains are provided for industrial fermentation and production of malic acid.

2. The *Aspergillus niger* strain of the disclosure can be applied to production of L-malic acid, after this strain is fermented for 5 days under the condition of a shaker, the yield of L-malic acid is 93.56-98.16 g/L which is improved by 1.97% compared with the starting strain, and the content of fumaric acid is 0.07-0.14 g/L which is reduced by 93.9% compared with the starting strain. Good strains are provided for preparing malic acid using the microbiological fermentation method.

3. The starting strain used in the disclosure is an *Aspergillus niger* malic acid high-yield strain S489. The *Aspergillus niger* strain is an *Aspergillus niger* strain in which the fumarate hydratase gene fum is knocked out on the basis of S1149.

DETAILED DESCRIPTION OF PREFERRED EMBODIMENTS

Figure 1:
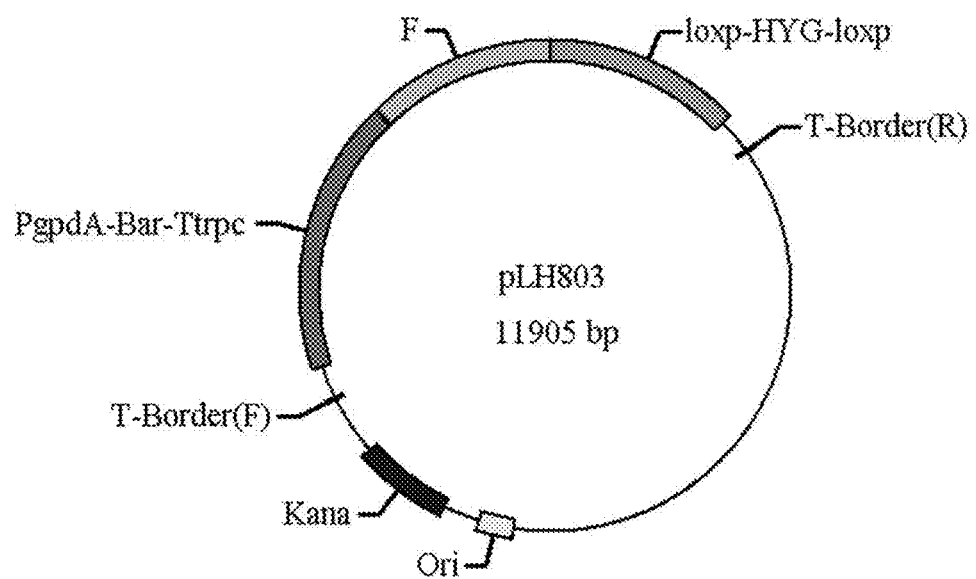
FIG. 1 is a map of a vector pLH803 constructed in the disclosure for knocking out a fum gene linked homologous right arm.

To better understand the disclosure, the disclosure will be further described in detail in combination with embodiments. However, the scope claimed by the disclosure is not limited to the scope represented by embodiments.

Raw materials used in the disclosure, unless otherwise noted, are all conventional commercially available products. The methods used in the disclosure, unless otherwise noted, are all conventional methods in the art. The masses of various substances used in the disclosure are conventional use masses.

An *Aspergillus niger* engineered strain for reducing byproduct fumaric acid in a fermentation process of L-malic acid is an *Aspergillus niger* engineered strain in which a fumarate hydratase gene fum is knocked out.

Preferably, the gene sequence of the fumarate hydratase gene fum is SEQ NO:1, and the amino acid sequence of the fumarate hydratase gene fum is SEQ NO:2.

Preferably, the fumarate hydratase gene fum is NCBI-locus_tagANI_1_952104.

A method for constructing the *Aspergillus niger* engineered strain for reducing byproduct fumaric acid in a fermentation process of L-malic acid as described above comprises the following steps:

(1) Construction of a Fumarate Hydratase Gene fum Knockout Vector respectively amplifying upstream and downstream sequence fragments of a gene fum through PCR reaction with a wild type *Aspergillus niger* ATCC1015 genome as a template, and recovering PCR products to respectively obtain target fragments; and cloning the upstream and downstream sequence fragments of the gene fum onto a vector pLH594, so as to construct a fumarate hydratase gene fum knockout vector pLH804;

wherein the upstream sequence of the gene fum is SEQ NO:3, and the downstream sequence of the gene fum is SEQ NO: 4;

(2) Obtaining of an *Aspergillus niger* Fumarate Hydratase Gene fum Knockout Strain:

transferring the vector pLH804 into an *Aspergillus niger* malic acid high-yield strain S1149, and conducting transformant screening and hygromycin resistance gene recombination to obtain an *Aspergillus niger* fumarate hydratase gene fum knockout strain M1.

A method for fermenting L-malic acid by utilizing the *Aspergillus niger* engineered strain as described above comprises the following steps:

inoculating the *Aspergillus niger* engineered strain into a PDA culture medium to be cultured for 5 days at 28° C. until conidia are generated, collecting the conidia and inoculating a conidium suspension into a fermentation culture medium, wherein the concentration of the conidia is $1*10^8$ conidia/50 ml, and then culturing for 5 days at a constant temperature of 28° C. at 200 rpm to obtain L-malic acid.

Preferably, the components and a formulation method of the fermentation culture medium are as follows:

100 g/L of glucose, 6 g/L of bacterial peptone, 0.15 g/L of anhydrous potassium dihydrogen phosphate, 0.15 g/L of anhydrous dipotassium hydrogen phosphate, 0.1 g/L of calcium chloride dihydrate, 0.1 g/L of magnesium sulfate heptahydrate, 0.005 g/L of sodium chloride, 0.005 g/L of ferrous sulfate heptahydrate and 0.001 g/L of anhydrous citric acid, a solvent is water, and autoclaving is performed for 20 min at 115° C.

Preferably, the yield of the L-malic acid obtained by the method is 93.56-98.16 g/L which is improved by 1.97% compared with a starting strain, and the yield of the fumaric acid is 0.07-0.14 g/L which is reduced by 93.9% compared with the starting strain.

Provided is use of the *Aspergillus niger* engineered strain as described above in production of L-malic acid.

Specifically, relevant preparation and detection are as follows:

Example 1: Construction of an *Aspergillus niger* fum Gene Knockout Strain

This example includes the following steps:

(1) Construction of a fum Gene Knockout Vector

Figure 2:
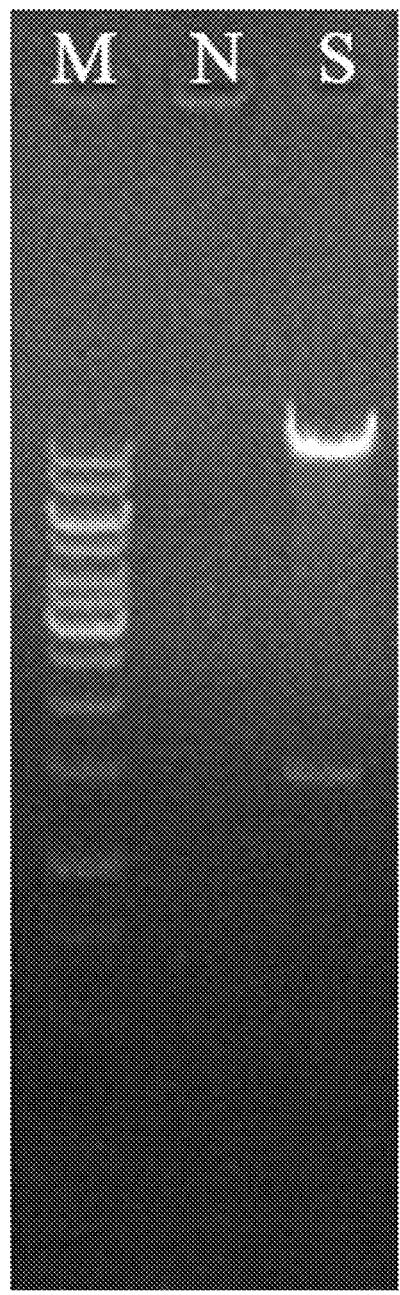
FIG. 2 is a double digestion validation diagram of a knockout vector pLH803 in the disclosure; wherein, M is DNA Marker, N is negative control, and S is a Sac I and Spe I double digestion validation vector.

To amplify the upstream sequence fragment of the fum gene, an *Aspergillus niger* ATCC1015 genome was used as a template to design amplification primers fum-F-F and fum-F-R, the upstream sequence fragment of the fum gene was recovered by PCR amplification, subjected to EcoR I and Sac I double digestion and glue recovery and then linked to a vector pLH594 obtained by the same restriction enzyme by virtue of One-Step Clone Kit, the linked product was transformed into *E. coli* JM109 competent cells and then evenly coated in an LB solid culture medium containing 100 µg/mL kanamycin resistance and inverted overnight at 37° C., and monoclones were picked to be subjected to colony PCR validation and plasmid double-digestion validation (FIG. 2) so as to obtain a vector pLH1066 successfully linked to the upstream sequence fragment of the fum gene, whose map is shown in FIG. 1.

Figure 3:
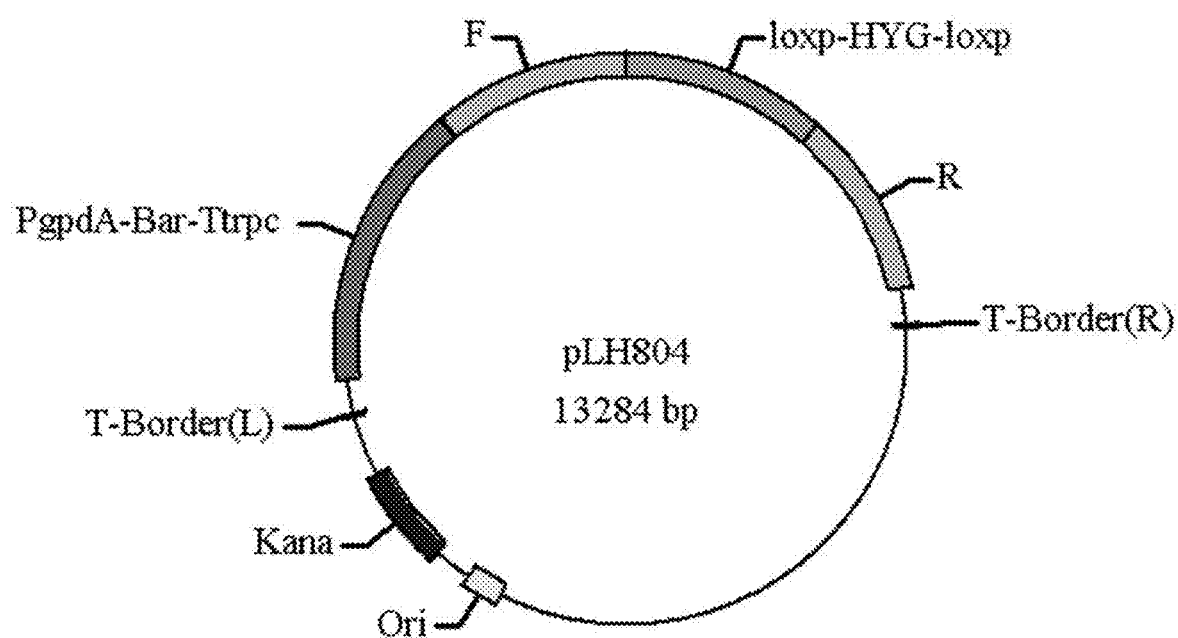
FIG. 3 is a map of a vector pLH803 constructed in the disclosure for knocking out fum gene linked homologous left and right arms.
Figure 4:
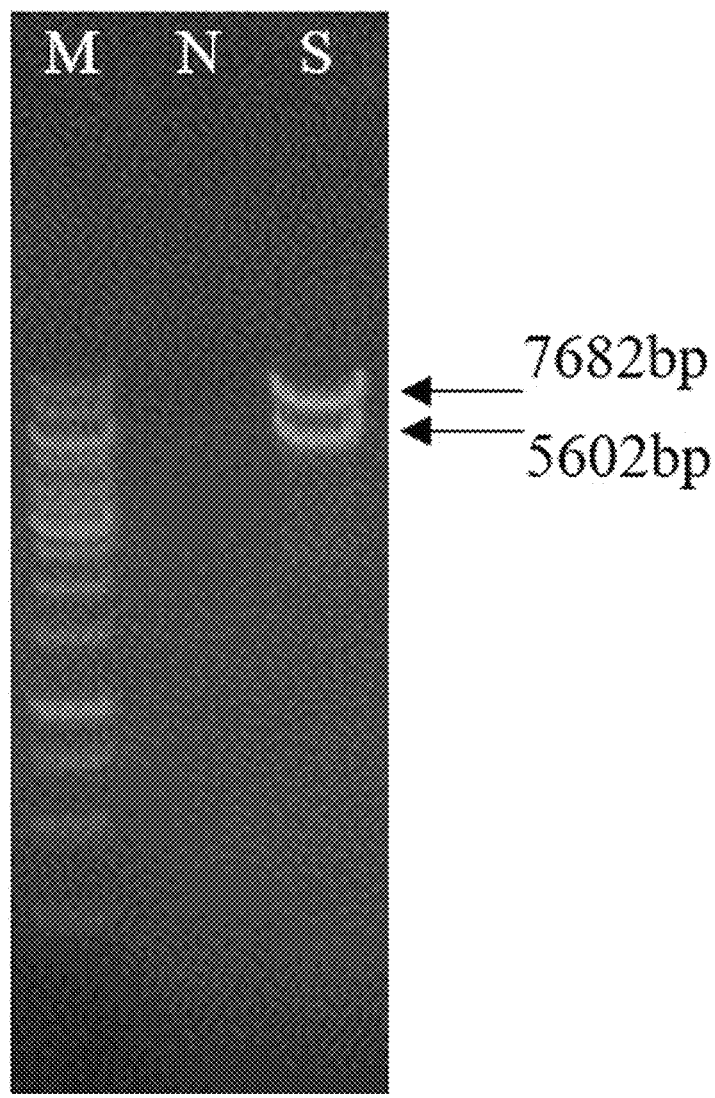
FIG. 4 is a double digestion validation diagram of a knockout vector pLH803 in the disclosure; wherein, M is DNA Marker, N is negative control, and S is Hind III digestion validation vector.

To amplify the downstream sequence fragment of the fum gene, an *Aspergillus niger* genome was used as a template to design amplification primers fum-R-F and fum-R-R, the downstream sequence fragment of the fum gene was recovered by PCR amplification, subjected to Xba I and Spe I double digestion and glue recovery and then linked to a vector pLH803 obtained by the same restriction enzyme by virtue of One-Step Clone Kit, the linked product was transformed into *E. coli* JM109 competent cells and then evenly coated in an LB solid culture medium containing 100 µg/mL kanamycin resistance and inverted overnight at 37° C., and monoclones were picked to be subjected to colony PCR validation and plasmid double-digestion validation (FIG. 4) so as to obtain a vector pLH804 successfully linked to the downstream sequence fragment of the fum gene, whose spectrum is shown in FIG. 3.

Figure 5:
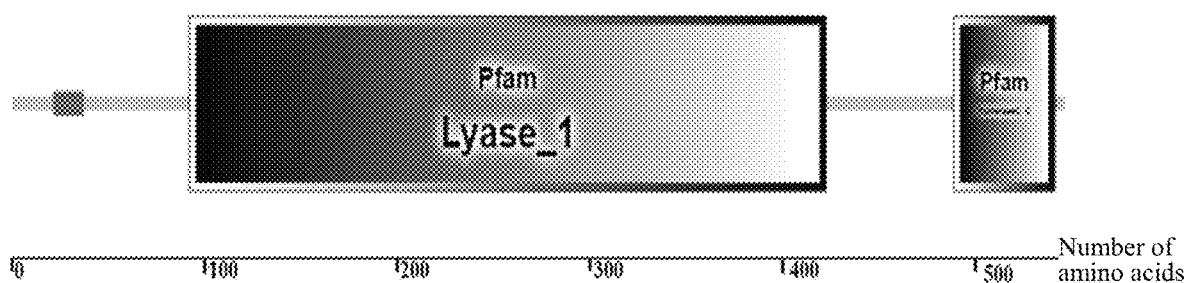
FIG. 5 shows a protein domain of a fum gene in the disclosure.

A protein functional domain of a fum gene is shown in FIG. 5.

Amplification primers are seen in Table 1.

TABLE 1

Primer sequence

| Primer name | Primer sequence (5'→3')[a] |
|---|---|
| fum-F-F | GCTCCGTAACACCCA<u>GAATTC</u>CCCAGCCAAGTATGCCATTG |
| fum-F-R | CGAAGTTATGGATCC<u>GAGCTC</u>GGATGTGTGCAAGGGATTGG |
| fum-R-F | GCTATACGAAGTTAT<u>TCTAGA</u>GCTTGGAGGAGTCATCTAGCG |
| fum-R-R | TGCCTGCAGGGGCCC<u>ACTAGT</u>TCTCCAATCCAGCACGCTTG |
| P1 | CCACTTCACAACAGCATCCC |
| P2 | CATCATCACGCGCGTTAGT |
| P3 | CTCTGAGCGAGGAGGACTT |
| P4 | CAGATTACCTCCAGCCATCC |
| P641 | CAATATCAGTTAACGTCGAC |
| P642 | GGAACCAGTTAACGTCGAAT |

[a]Underline sequence represents restriction enzyme sites

The gene sequence of the gene fum is SEQ NO:1, with a length of 2384 bp; the amino acid sequence of the gene fum is SEQ NO:2, with 547 amino acids; the functional domain of a protein is shown in FIG. 5.

The upstream sequence of the fum gene is SEQ NO:3, with a length of 1443 bp;

The downstream sequence of the fum gene is SEQ NO:4, with a length of 1379 bp;

The LB solid culture medium containing kanamycin resistance comprises the following components: 10 g/L of tryptone, 5 g/L of yeast extract, 10 g/L of sodium chloride and 15 g/L of agar powder. Sterilization was performed for 20 min at 121° C. Kanamycin was added when sterilizing and cooling to about 50° C. until a final concentration was 100 µg/mL.

(2) Obtaining of an *Aspergillus niger* fum Gene Knockout Strain

Figure 6:
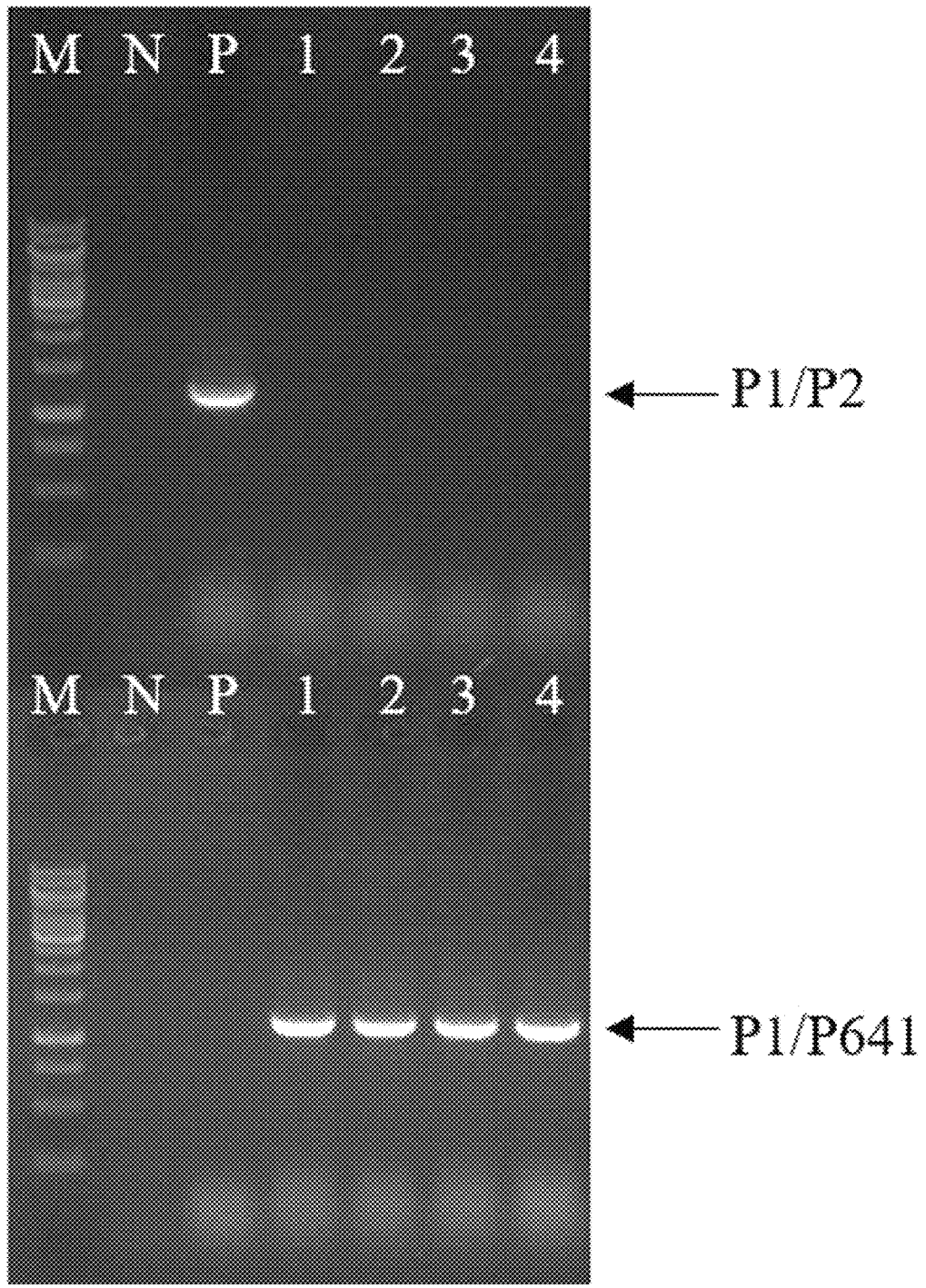
FIG. 6 is a PCR validation diagram of a fum gene knockout left homologous right arm, primers P1 and P2 verify a left homology arm, and primers P1 and P641 verify a left homology arm-php; wherein M is DNA Marker, N is Negative control, P is positive control, and 1-4 is an *Aspergillus niger* transformant genome in which a fum gene is successfully knocked out.
Figure 7:
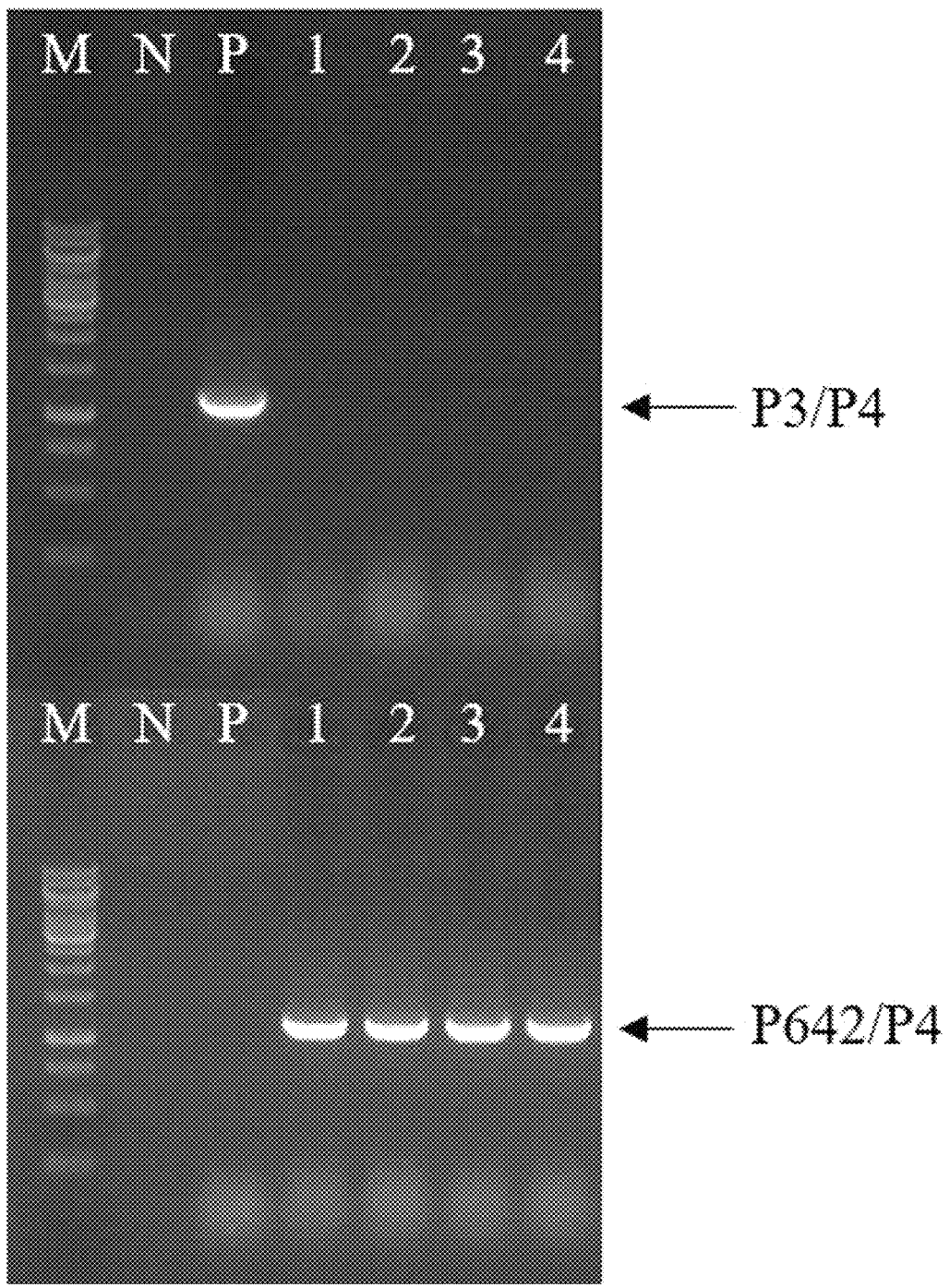
FIG. 7 is a PCR validation diagram of a fum gene knockout right homology arm in the disclosure, primers P3 and P4 verify a right homology arm, and primers P642 and P4 verify a right homology arm-php; wherein, M is DNA Marker, and N is Negative control, P is a positive control, and 1-4 is an *Aspergillus niger* transformant genome in which a fum gene is successfully knocked out.

The vector pLH804 was electroporated into *agrobacterium*, then this *agrobacterium* containing a corresponding vector and an *Aspergillus niger* host strain S489 were co-cultured in an TIM culture medium for *agrobacterium*-mediated transformation, the culture product was evenly coated in a CM culture medium after culturing for 2.5 days to be cultured until transformants were grown, and then the transformants were screened, the phenotypes of the transformants are insensitive to hygromycin resistance and sensitive to glufosinate-ammonium. Such the transformants were subjected to genome validation and validation primers were designed (Table 1). Amplification results satisfy that the amplification of left and right homology arms is negative (FIG. 6), the amplification of left and right homology arms-php is positive (FIG. 7), one of the correct fum knockout clones was picked for induction and recombination of resistance marker hygromycin, so as to obtain a fum knockout strain M1 without hygromycin resistance.

The transformation method of the gene knockout is an *agrobacterium*-mediated method.

The electrotransformation conditions of the *agrobacterium*-mediated method are as follows: Capacitance: 25 uF, Voltage: 2.5 kV, Resistance: 200Ω, Pulse: 5 msec.

The *Agrobacterium* strain is an AGL-1 strain.

A method for formulating the IM culture medium comprises: water was added into 15 g of agar so that a 905.7 mL volume was reached, sterilization was performed at 121° C. for 20 min, 0.8 mL of sterile K buffer, 20 mL of MN buffer, 1 mL of 1% $CaCl_2 \cdot 2H_2O$, 10 mL of 0.01% $FeSO_4$, 5 mL of IM Trace elements, 2.5 mL of 20% $NH_4NO_3$, 10 mL of 50% glycerol, 40 mL of IM MES and 5 mL of 20% glucose which were prepared in advance were added, kanamycin was added when the temperature was reduced to about 50° C. so that a final concentration was 100 µg/mL, acetosyringone was added so that the final concentration was 200 µM.

A method for formulating the CM culture medium comprises: water was added into 20 g of agar so that a 897 mL volume was reached, sterilization was performed at 121° C. for 20 min, 20 mL of aseptic ASP+N, 20 mL of 50% glucose, 2 mL of 1M $MgSO_4$, 1 mL of CM Trace elements, 10 mL of 10% casein hydrolyzate and 50 mL of 10% yeast extract which were prepared in advance were added, hygromycin was added when the temperature was reduced to about 50° C. so that the final concentration was 250 µg/mL, streptomycin was added so that the final concentration was 100 µg/mL, cefotaxime sodium was added so that the final concentration was 100 µg/mL, and ampicillin was added so that the final concentration was 100 µg/mL.

The validation primer sequences are seen in Table 1.

The induction and recombination method of the resistance marker comprises: spores of about 400 fum gene knockout clones were evenly coated onto an MM culture medium containing 30 µg/mL tetracycline, cultured at 28° C. until monoclones were grown, and 100 monoclones were randomly picked and transferred to a PDA culture medium to be cultivated at 28° C. for 24 h, and then the clones were transferred to a PDA medium containing hygromycin for 24 h at 28° C. one by one, and finally the phenotypes were observed to screen the transformants induced and recombined by resistance markers, that is, the transformants which can be normally grown in the PDA culture medium but cannot be normally grown in the PDA culture medium containing hygromycin were successfully induced and recombined transformants

Example 2: Use of an Engineered Strain in Production of L-Malic Acid Via Fermentation A method for producing malic acid by utilizing the *Aspergillus niger* fum gene knockout engineered strain M1 constructed in the disclosure in a shaker via fermentation specifically comprises the following steps:

First, the obtained engineered strain M1 was inoculated into a PDA culture medium and subjected to inverted culture in a 28° C. incubator for 5 days until enough conidia were generated;

a method for formulating the PDA culture medium comprises: 200 g of peeled potatoes were accurately weighed and cut into about 1 $cm^3$ of small pieces, distilled water was added, the resulting mixture was boiled for 30 min under the condition of continuous stirring and filtered with double-layer gauze, filtrate was collected, 20 g of glucose was stirred until it was completely dissolved, the volume was adjusted to 1 L with distilled water, the resulting mixture was packaged into a jar, 1.5% agar was added, and the jar was autoclaved at 121° C. for 20 min. 1.5% of agar was added in the solid culture medium.

Then, the conidia of strains M1 were collected and inoculated into a malic acid fermentation culture medium, wherein the final concentration of the conidia was $1*10^8$ conidia/50 mL, and the shaker was placed under the conditions of 28° C. and at 200 rpm for 5 days of culture.

The malic acid fermentation culture medium comprises the compositions: 100 g/L of glucose, 6 g/L of bacterial peptone, 0.15 g/L of anhydrous potassium dihydrogen phosphate, 0.15 g/L of anhydrous dipotassium hydrogen phosphate, 0.1 g/L of calcium chloride dihydrate, 0.1 g/L of magnesium sulfate heptahydrate, 0.005 g/L of sodium chloride, 0.005 g/L of ferrous sulfate heptahydrate and 0.001 g/L of anhydrous citric acid. Autoclaving was performed for 20 min at 115° C.

Figure 8:
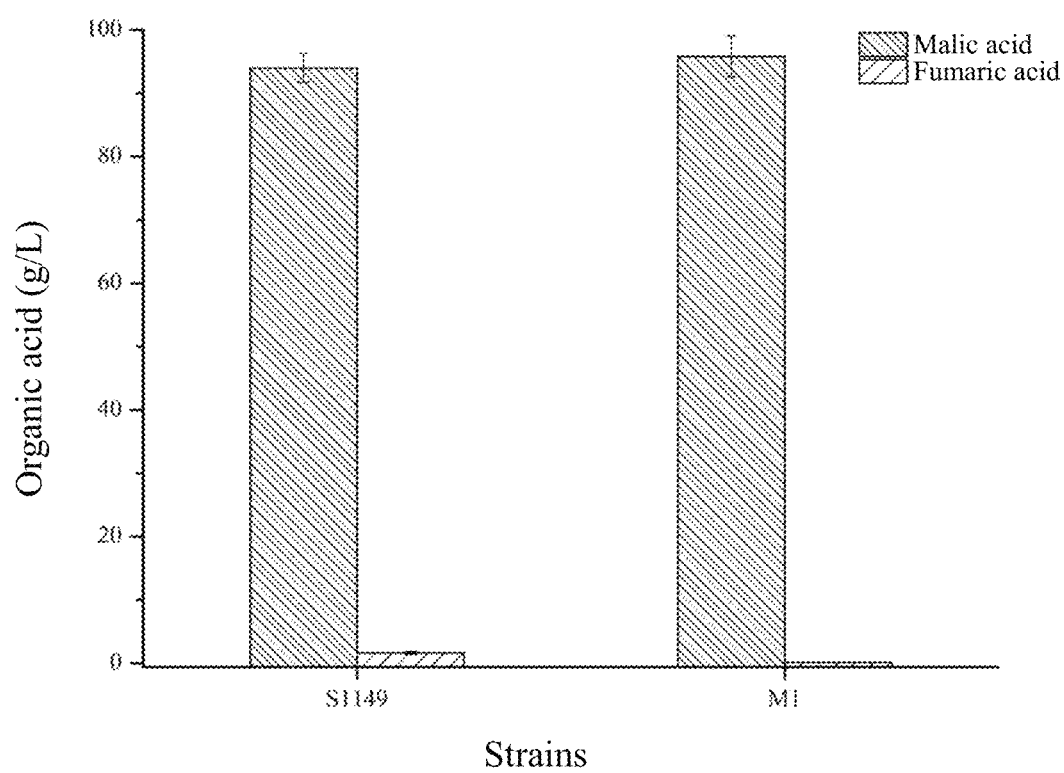
FIG. 8 is a graph showing an organic acid yield of an engineered strain constructed in the disclosure after being fermented in a shaker; S489 is an organic acid yield of a starting strain on day 5, and M1 is an organic acid yield of a fum gene knockout strain on day 5.

Finally, the fermentation product was collected to prepare a test sample, and the content of the main organic acid in the sample was determined by HPLC. The results showed that the main organic acid was malic acid, the content of the byproduct fumaric acid was significantly reduced. The results are shown in FIG. 8.

A method for preparing the detection sample comprises: 2 mL of evenly vibrated fermentation broth was sucked, an equal volume of 2 M HCl was added, the above materials fully reacted, the reaction product was centrifuged to take supernatant, the supernatant was diluted by 50 folds, and the diluted supernatant was filtered via a 0.22 µm filter membrane and then stored in a liquid vial for future HPLC analysis.

A method for detecting an organic acid via HPLC comprises: Agilent high performance liquid chromatograph UV detector, AminexHPX-87H chromatographic column (300 mm*7.8 mm), 5 mM $H_2SO_4$ mobile phase, 0.6 mL/min flow rate, the column temperature was 65° C., the detection wavelength was 210 nm, and the injection volume was 20 µL.

According to research results of the disclosure, the byproduct fumaric acid accumulated in the production process of malic acid through fermentation of *Aspergillus niger* is greatly reduced, the cost in the process of downstream separation and purification malic acid was reduced, and good strains are provided for industrialized production of malic acid via fermentation.

The sequences used in the disclosure are as follows:

```
SEQ NO: 1:
ttgccgtcccccaggttttgggtagaattggaatatcattagatctgtcgtcttatattgtttattttagagagataaagtacg accaatcccttgcacacatcctcgacaggatgtgaattgtttcccaaaaaatggcaccattggttagccagccacacacagtgactaa cgcgcgtgatgatgaatagatccagaagccggtcgtcatgttgacatctgcccacacttcccgagccgcggtgcgctcgatggcct ccttgacacatgctgcatctcgagcttcggcttccccgcagttgccgcactgccgtcgctttcaccccgcctcgttcagttgccgt cgtcttctgagctccaatagccgacctgttcaacacttccccgtcttcagaccttgacttccacctccagcaagagagcctttggcac
```

-continued

```
caccgtcaagatggtatgctctatcctttccattgaatcgcatctatcatatggatgacttcgctatggggaaagagccccaactgcga
gacgttgctaatcggttattgttttagtcttcggctacccgcattgagaccgatgccttcggtgagatcgaggtatgtgctacactgatg
cacacgatgcgtatagaatgcgaatgctgactgcttttcttttctaggtccccgccgacaagtactggggtgcccagacccagcggt
aagaccccgatttcaacaatcgctgccacactgcaaactggctatgcgaccgatacacgaagtgagcagatgctgactggcgcga
caatagctccctgggcaacttcgacatcaaccagccccaggaccgcatgcctgagcccgttgtcaaggctttcggtatcctcaagg
gtgctgctgctgaagtgaacatgaagttcggccttggtaagccgctatcgattaaagcagcacagctccggcgaagttaacaccag
gaaattagaccccaagatcggcgaggccatcaagcaggctgccgccgaggttgcggagggcaagctgatggaccacttcccccct
cgtcgtctggcagaccggttccggtacccagtccaacatgaactcgaacgaggtcatctccaaccgcgccattgagatcctgggcg
gcgagaagggctccaagaagcccgtccaccccaacgaccacgtcaacatgtccgcctcctccaatgactccttcccgaccgctat
gcacattgctgccgttgtggagctggagaacaccctcctgccttccctgaggagcctgcgcgatgctctccaggtcaaggttgaga
agttcgacaagatcatcaagatcggtcgtactcacctgcaggacgccacccctctcaccctcggtcaggagttctccggctacgtcg
ctcagctcgaccgcaacattgagcgtgtcgagactagcatcccccacctccgctacctggctcagggtggtaccgccgtcggtact
ggtctgaacaccttcaagggcttcgacgaggctatcgctgctgaggtcaccaagttgaccggcaccgagttcaagactgcccccaa
caagttcgaggttctggccgcccacgactcgattgtcgaggcttccggtgccctgaacaccctggcctgctctctgttcaagattgcc
caggacatccgttaccttggatccggtccccgctgcggtcttggtgaactggtcctccccgagaacgagcctggctcttccatcatg
cccggcaaggttaaccccactcagtgcgagtcccttaccatggtctgctcccaggtcatgggtaaccacgtcgctgccactgtcgg
cggcatgaacggtcagttcgagctcaacgtgttcaagcccctcatgatccgcaacctgctgcacagcgtgcgcatcctggccgatg
gcatggccagcttcgagaagaacctggtgcacggtctggaggccaacgagccccgcatcaactctctcctccacgagaggtatgt
atttccctaaaaaatcggacctttgtaaagaagacaactaacggtggtgagtctgatgttggtcacctgcctgaacccgtcattggc
tacgacatggcctccaaggtcgccaagaacgcccacaagaagggcctcactctgaagcagagtgctatggagctgaaggctctg
agcgaggaggactttgacaagtacgtccgcccggagctgatgctgagccccaaggagaagaaataaatgtatagcgggacgag
agatgttttggcttagcttggaggagtcatctagcgaagactagcttttgcctaggagatatttgtatactcaggaatactactgtacta
ttcttcttgttcagcttattgcttggatagagttcttcgctgtacgg
```

SEQ NO: 2:
MetLeuThrSerAlaHisThrSerArgAlaAlaValArgSerMetAlaSerLeuThrHisAlaAlaSer

ArgAlaSerAlaSerProAlaValAlaArgThrAlaValAlaPheThrProAlaSerPheSerCysArg

ArgLeuLeuSerSerAsnSerArgProValGlnHisPheProArgLeuGlnThrLeuThrSerThrSer

SerLysArgAlaPheGlyThrThrValLysMetSerSerAlaThrArgIleGluThrAspAlaPheGly

GluIleGluValProAlaAspLysTyrTrpGlyAlaGlnThrGlnArgSerLeuGlyAsnPheAspIle

AsnGlnProGlnAspArgMetProGluProValValLysAlaPheGlyIleLeuLysGlyAlaAlaAla

GluValAsnMetLysPheGlyLeuAspProLysIleGlyGluAlaIleLysGlnAlaAlaAlaGluVal

AlaGluGlyLysLeuMetAspHisPheProLeuValValTrpGlnThrGlySerGlyThrGlnSerAsn

MetAsnSerAsnGluValIleSerAsnArgAlaIleGluIleLeuGlyGlyGluLysGlySerLysLys

ProValHisProAsnAspHisValAsnMetSerAlaSerSerAsnAspSerPheProThrAlaMetHis

IleAlaAlaValValGluLeuGluAsnThrLeuLeuProSerLeuArgSerLeuArgAspAlaLeuGln

ValLysValGluLysPheAspLysIleIleLysIleGlyArgThrHisLeuGlnAspAlaThrProLeu

ThrLeuGlyGlnGluPheSerGlyTyrValAlaGlnLeuAspArgAsnIleGluArgValGluThrSer

IleProHisLeuArgTyrLeuAlaGlnGlyGlyThrAlaValGlyThrGlyLeuAsnThrPheLysGly

PheAspGluAlaIleAlaAlaGluValThrLysLeuThrGlyThrGluPheLysThrAlaProAsnLys

PheGluValLeuAlaAlaHisAspSerIleValGluAlaSerGlyAlaLeuAsnThrLeuAlaCysSer

LeuPheLysIleAlaGlnAspIleArgTyrLeuGlySerGlyProArgCysGlyLeuGlyGluLeuVal

-continued

LeuProGluAsnGluProGlySerSerIleMetProGlyLysValAsnProThrGlnCysGluSerLeu

ThrMetValCysSerGlnValMetGlyAsnHisValAlaAlaThrValGlyGlyMetAsnGlyGlnPhe

GluLeuAsnValPheLysProLeuMetIleArgAsnLeuLeuHisSerValArgIleLeuAlaAspGly

MetAlaSerPheGluLysAsnLeuValHisGlyLeuGluAlaAsnGluProArgIleAsnSerLeuLeu

HisGluSerLeuMetLeuValThrCysLeuAsnProValIleGlyTyrAspMetAlaSerLysValAla

LysAsnAlaHisLysLysGlyLeuThrLeuLysGlnSerAlaMetGluLeuLysAlaLeuSerGluGlu

AspPheAspLysTyrValArgProGluLeuMetLeuSerProLysGluLysLys

SEQ NO: 3:
CCCAGCCAAGTATGCCATTGCCTACGGCCGTGCTCAAGGTCCTGATGTC

TTCCGCATCACGGAGCAGAAATGTCCCGTGCAAGGGGGCGAGATAACCATCCG

TATCTTCGAGCCTGCCCCGAAAGCGGATGAGCATGGCAAGGCCAAAAAGAGGG

CTGCGTTTGTCAACTTCCATGGGGAGGCTGGGTGTTCGGCGATCTCTCAGTTG

ATCACGATTTCTGCAAGACACTCGTCGATGGCCTGGACGGGCACTTGGTCGCGT

TTGATGTCGACTACCGGCTAGCTCCTGAGCACAAGTACCCGATCCCCGTTGACG

ACTGCTGGACCGCTTTCAATTGGGTCAGCTACAACTCCCTGTCTACATCGACCG

GTATGGTCAATACTAACTGACATCCCGTGCAGATCCGCTCCCAGAAAGCAGAG

GAGTTCAACGTTGACCCGAATCGAATAGCTGTTGGAGGTTGTTCGGCCGGAGG

CCACCTGTCAGCCGTGGTCGCTCATCTCTGCCGTAATGGCGGCATTCCGTTGCG

CCTGCAGGTGCTGAACGTGCCCGTATGTGATCTACATAGCGGCTACACTCCGGA

TGGTGAATTCGATCGGGAGAACTGTCCCTATGAGTCCTACAGAGAGATGGAGT

TCACCGCAGCTCTTCCGGTAGCACGGATGGCTTATTTCCATCGACACTTTTTGG

GGGTTCCCCGGCCAGCACGTTCAGAAGAGGTAAGTAGTACCGTAATTGCTGCA

GCCGGAGCTGCACACAACTGCAAGATGCTGATGTGATCCATAGGACTGGAAGA

TCTCCCCCATATTTGCGCCTGACTTTTCTGGACTAGCACCTGCGTTGGTCTTCAC

CGCCGAAATGGATCCTCTGCGGGACGAAGGGGAGGCCTACGCTGCCAAATTGA

AAGCTGGCGGTTGTCGAGTGGAAATGATGCGTATGGCAGGAGCACCCCACACA

TTTGCCATGTTGGATGGCATCTTAGAGAGCGGCCGTATATATACCGAGAAGGTC

ATCGAAGCGATGAAACGGGAACTAACAGGGTAAATAATCAATTGGTTCGGTTG

AAGGGATATCGAAGATGGAGAGCAGTGTTAGTGCAGAGCGACTAGAAGATGG

AAATGCGGAGAGACAGCAGGATCATGGTTTATCCGACGAGAATCTTTACCGTA

TGATACCATTTAGGCCGGGCAGCGAAGGTGTGGCAGACGGGTAACCGGCGTCC

TGAACATTACCGGGCCGGGAGATTTCGGCAGGCGGTATCGGAAACAGTTGGGG

TGGATTAAATATGCGCGGCTGCTGCTGCTCTTCTTCTTCCCTTCTTTTCTGCGTG

GTTTGTTTGCCGTCCCCAGGTTTTGGGTAGAATTGGAATATCATTAGATCTGTC

GTCTTATATTGTTTATTTTAGAGAGATAAAGTACGACCAATCCCTTGCACACAT

CC

SEQ NO: 4:
GCTTGGAGGAGTCATCTAGCGAAGACTAGCTTTTGCCTAGGAGATATTT

GTATACTCAGGAATACTACTGTACTATTCTTCTTGTTCAGCTTATTGCTTGGATAG

AGTTCTTCGCTGTACGGAGTATAGAATTTTCTCGGGCTGATGACGGGGCTGACCC

CGGGGTGTGCTATTTTTGGACCACCAAAGCGGTCCCGCCCACCGATCGAATAGT

TCAAGATGCACGGATAGCAACGACTGACGGTGTGTTGCTGAGGGCCAGTCAAG

-continued

```
TGGTGTTAAATTTAGGCATACTAACTAGTAACGTTGCTGCGCCAGTCAGGCTTGG

AGGGTGATCGGCTTGACCAGTGCCAGTCGGAAAGAACCGTATGTAGTGGTAAGT

AGTAAGTAGTCAGGGGCGGATTTCCAAAGTGTTTGGTGTTTCAGGCAAACCGTG

GGCCCTTCTCTTACTGCTTGTTTATTACCTCCGCCTGGCCCTTTCTTTTCCATCAC

CGACTGACCGACTGACTCGATTGACCTGTCCTTTTTTTCCCTTCATCCCTTTCCC

CCTCAAATACTCACCTTCGTTGGAAATACTCTGTCTTTCGTTCAAACACTCACTA

TCACTGAAGAAATCCTTCATTCCAGCGTTTCAATAATTCCCATCCGTTTTCACCA

CTCAATTGAACCCCGCCACTAACCAGGGGCCCTTCCTCCCTTAACTAAACTACC

AAACAACCTCTTCACGAAACTCCTCAAAGCCTTTTTCTCCTCTCCAGCAAAAAG

TTCAAGACGGACAAAAAACATACCACCGCCAACATGACCAACGCCTCCACCCT

CACCCAACCCCCGCCGAATCCAAGGACGACGCCCCCCTCTTCCCTACGACCCT

CATCTCCCCCTCCGTCGCCGCCGAACTGCCCGAAGGCTACAAGATCCGTCCCGT

CCGTCGCTCCGACTACAGCCGCGGCTACCTGGACGTGTTGCGCGTGCTGACGAC

CGTCGGCACCATCACCGAGGAGCAGTGGAACAAGCGCTACGACTGGATCTCGT

CGCGCAATGACGAGTACTACCTGCTTGTTATCTGTGACGGGGAGGATCGTGTCG

TGGGCACGGGCAGCTTGATTGTTGAGCGCAAGTTCATTCATGAGTTGGGTCTTG

TGGGCCATATTGAGGACATTGCCGTCGAGAAGGGCCAGCAGGGGAAGAGGCTC

GGGCTGAGGCTTATTCAGGCGTTGGATTATGTTGCGGCGCAGGTGGGATGCTAC

AAGGTATGTCTTCTACTTCTTATTATGGGAGTGGTGGTCGTCATGATGCTAATGGT

CAATGCAGAGTATTCTCGATTGCTCCGAGGCGAATGAGGGATTCTACCTCAAGT

GCGGCTTCAAGCGTGCTGGATTGGAGA
```

Although the embodiments of the disclosure have been disclosed for illustrative purposes, those skilled in the art will appreciate that various substitutions, changes and modifications are possible without departing from the spirit and scope of the disclosure and the appended claims, and therefore the scope of the disclosure is not limited to the contents disclosed in the embodiments.

SEQUENCE LISTING

```
<110> Nanjing Haohe Biotechnology Co., Ltd
<120> METHOD AND STRAINS FOR REDUCING BYPRODUCT FUMARIC ACID IN
A FERMENTATION PROCESS OF L-MALIC ACID, AND USE THEREOF.
<160>   14
<170> SIPOSequenceListing 1.0
<210>    1
<211> 2384
<212> DNA
<213> Gene sequence of fumaric acid hydratase gene fum (Unknown)
<400>    1
ttgccgtccc ccaggttttg ggtagaattg gaatatcatt agatctgtcg tcttatattg    60
tttattttag agagataaag tacgaccaat cccttgcaca catcctcgac aggatgtgaa   120
ttgtttccca aaaaatggca ccattggtta gccagccaca cacagtgact aacgcgcgtg   180
atgatgaata gatccagaag ccggtcgtca tgttgacatc tgcccacact tcccgagccg   240
cggtgcgctc gatggcctcc ttgacacatg ctgcatctcg agcttcggct tccccccgcag  300 ttgcccgcac tgccgtcgct ttcaccccg cctcgttcag ttgccgtcgt cttctgagct   360
ccaatagccg acctgttcaa cacttccccc gtcttcagac cttgacttcc acctccagca   420
agagagcctt tggcaccacc gtcaagatgg tatgctctat cctttccatt gaatcgcatc   480
tatcatatgg atgacttcgc tatggggaaa gagccccaac tgcgagacgt tgctaatcgg   540
ttattgtttt agtcttcggc tacccgcatt gagaccgatg ccttcggtga gatcgaggta   600
```

-continued

```
tgtgctacac tgatgcacac gatgcgtata gaatgcgaat gctgactgct tttcttttct    660
aggtccccgc cgacaagtac tggggtgccc agacccagcg gtaagacccc gatttcaaca    720
atcgctgcca cactgcaaac tggctatgcg accgatacac gaagtgagca gatgctgact    780
ggcgcgacaa tagctccctg gcaacttcg acatcaacca gccccaggac cgcatgcctg     840
agcccgttgt caaggctttc ggtatcctca agggtgctgc tgctgaagtg aacatgaagt    900
tcggccttgg taagccgcta tcgattaaag cagcacagct ccggcgaagt taacaccagg    960
aaattagacc ccaagatcgg cgaggccatc aagcaggctg ccgccgaggt tgcggagggc   1020
aagctgatgg accacttccc cctcgtcgtc tggcagaccg gttccggtac ccagtccaac   1080
atgaactcga acgaggtcat ctccaaccgc gccattgaga tcctgggcgg cgagaagggc   1140
tccaagaagc ccgtccaccc caacgaccac gtcaacatgt ccgcctcctc caatgactcc   1200
ttcccgaccg ctatgcacat tgctgccgtt gtggagctgg agaacaccct cctgccttcc   1260
ctgaggagcc tgcgcgatgc tctccaggtc aaggttgaga agttcgacaa gatcatcaag   1320
atcggtcgta ctcacctgca ggacgccacc cctctcaccc tcggtcagga gttctccggc   1380
tacgtcgctc agctcgaccg caacattgag cgtgtcgaga ctagcatccc ccacctccgc   1440
tacctggctc agggtggtac cgccgtcggt actggtctga acaccttcaa gggcttcgac   1500
gaggctatcg ctgctgaggt caccaagttg accggcaccg agttcaagac tgcccccaac   1560
aagttcgagg ttctggccgc ccacgactcg attgtcgagg cttccggtgc cctgaacacc   1620
ctggcctgct ctctgttcaa gattgcccag gacatccgtt accttggatc cggtccccgc   1680
tgcggtcttg gtgaactggt cctccccgag aacgagcctg gctcttccat catgcccggc   1740
aaggttaacc ccactcagtg cgagtccctt accatggtct gctcccaggt catgggtaac   1800
cacgtcgctg ccactgtcgg cggcatgaac ggtcagttcg agctcaacgt gttcaagccc   1860
ctcatgatcc gcaacctgct gcacagcgtg cgcatcctgg ccgatggcat ggccagcttc   1920
gagaagaacc tggtgcacgg tctggaggcc aacgagcccc gcatcaactc tctcctccac   1980
gagaggtatg tatttcccta aaaaatcgga ccttttgtaaa gaagacaact aacggtggtg   2040
tagtctgatg ttggtcacct gcctgaaccc cgtcattggc tacgacatgg cctccaaggt   2100
cgccaagaac gcccacaaga agggcctcac tctgaagcag agtgctatgg agctgaaggc   2160
tctgagcgag gaggactttg acaagtacgt ccgcccggag ctgatgctga gcccaaggga   2220
gaagaaataa atgtatagcg ggacgagaga tgttttggct tagcttggag gagtcatcta   2280
gcgaagacta gcttttgcct aggagatatt tgtatactca ggaatactac tgtactattc   2340
ttccttgttca gcttattgct tggatagagt tcttcgctgt acgg                   2384
```

<210> 2
<211> 547
<212> PRT
<213> Amino acid sequence of fumaric acid hydratase gene fum (Unknown)
<400> 2

```
Met Leu Thr Ser Ala His Thr Ser Arg Ala Ala Val Arg Ser Met Ala
 1               5                  10                  15

Ser Leu Thr His Ala Ala Ser Arg Ala Ser Ala Ser Pro Ala Val Ala
            20                  25                  30

Arg Thr Ala Val Ala Phe Thr Pro Ala Ser Phe Ser Cys Arg Arg Leu
        35                  40                  45

Leu Ser Ser Asn Ser Arg Pro Val Gln His Phe Pro Arg Leu Gln Thr
    50                  55                  60

Leu Thr Ser Thr Ser Ser Lys Arg Ala Phe Gly Thr Thr Val Lys Met
65                  70                  75                  80
```

```
Ser Ser Ala Thr Arg Ile Glu Thr Asp Ala Phe Gly Glu Ile Glu Val
                85                  90                  95

Pro Ala Asp Lys Tyr Trp Gly Ala Gln Thr Gln Arg Ser Leu Gly Asn
            100                 105                 110

Phe Asp Ile Asn Gln Pro Gln Asp Arg Met Pro Glu Pro Val Val Lys
            115                 120                 125

Ala Phe Gly Ile Leu Lys Gly Ala Ala Glu Val Asn Met Lys Phe
            130                 135                 140

Gly Leu Asp Pro Lys Ile Gly Glu Ala Ile Lys Gln Ala Ala Ala Glu
145                 150                 155                 160

Val Ala Glu Gly Lys Leu Met Asp His Phe Pro Leu Val Val Trp Gln
                165                 170                 175

Thr Gly Ser Gly Thr Gln Ser Asn Met Asn Ser Asn Glu Val Ile Ser
            180                 185                 190

Asn Arg Ala Ile Glu Ile Leu Gly Gly Glu Lys Gly Ser Lys Lys Pro
            195                 200                 205

Val His Pro Asn Asp His Val Asn Met Ser Ala Ser Ser Asn Asp Ser
    210                 215                 220

Phe Pro Thr Ala Met His Ile Ala Ala Val Val Glu Leu Glu Asn Thr
225                 230                 235                 240

Leu Leu Pro Ser Leu Arg Ser Leu Arg Asp Ala Leu Gln Val Lys Val
                245                 250                 255

Glu Lys Phe Asp Lys Ile Ile Lys Ile Gly Arg Thr His Leu Gln Asp
            260                 265                 270

Ala Thr Pro Leu Thr Leu Gly Gln Glu Phe Ser Gly Tyr Val Ala Gln
            275                 280                 285

Leu Asp Arg Asn Ile Glu Arg Val Glu Thr Ser Ile Pro His Leu Arg
    290                 295                 300

Tyr Leu Ala Gln Gly Gly Thr Ala Val Gly Thr Gly Leu Asn Thr Phe
305                 310                 315                 320

Lys Gly Phe Asp Glu Ala Ile Ala Ala Glu Val Thr Lys Leu Thr Gly
            325                 330                 335

Thr Glu Phe Lys Thr Ala Pro Asn Lys Phe Glu Val Leu Ala Ala His
            340                 345                 350

Asp Ser Ile Val Glu Ala Ser Gly Ala Leu Asn Thr Leu Ala Cys Ser
    355                 360                 365

Leu Phe Lys Ile Ala Gln Asp Ile Arg Tyr Leu Gly Ser Gly Pro Arg
    370                 375                 380

Cys Gly Leu Gly Glu Leu Val Leu Pro Glu Asn Glu Pro Gly Ser Ser
385                 390                 395                 400

Ile Met Pro Gly Lys Val Asn Pro Thr Gln Cys Glu Ser Leu Thr Met
            405                 410                 415

Val Cys Ser Gln Val Met Gly Asn His Val Ala Ala Thr Val Gly Gly
            420                 425                 430

Met Asn Gly Gln Phe Glu Leu Asn Val Phe Lys Pro Leu Met Ile Arg
            435                 440                 445

Asn Leu Leu His Ser Val Arg Ile Leu Ala Asp Gly Met Ala Ser Phe
    450                 455                 460

Glu Lys Asn Leu Val His Gly Leu Glu Ala Asn Glu Pro Arg Ile Asn
465                 470                 475                 480

Ser Leu Leu His Glu Ser Leu Met Leu Val Thr Cys Leu Asn Pro Val
            485                 490                 495

Ile Gly Tyr Asp Met Ala Ser Lys Val Ala Lys Asn Ala His Lys Lys
            500                 505                 510
```

```
        Gly Leu Thr Leu Lys Gln Ser Ala Met Glu Leu Lys Ala Leu Ser Glu
            515                 520                 525

Glu Asp Phe Asp Lys Tyr Val Arg Pro Glu Leu Met Leu Ser Pro Lys
            530                 535                 540

Glu Lys Lys
        545

<210> 3
<211> 1443
<212> DNA
<213> Upstream sequence of fum gene (Unknown)
<400> 3
cccagccaag tatgccattg cctacggccg tgctcaaggt cctgatgtct tccgcatcac      60
ggagcagaaa tgtcccgtgc aaggggggcga ataaccatc cgtatcttcg agcctgcccc    120
gaaagcggat gagcatggca aggccaaaaa gagggctgcg tttgtcaact tccatggggg    180
aggctgggtg ttcggcgatc tctcagttga tcacgatttc tgcaagacac tcgtcgatgg    240
cctggacggg cacttggtcg cgtttgatgt cgactaccgg ctagctcctg agcacaagta    300
cccgatcccc gttgacgact gctggaccgc tttcaattgg gtcagctaca actccctgtc    360
tacatcgacc ggtatggtca atactaactg acatcccgtg cagatccgct cccagaaagc    420
agaggagttc aacgttgacc cgaatcgaat agctgttgga ggttgttcgg ccggaggcca    480
cctgtcagcc gtggtcgctc atctctgccg taatggcggc attccgttgc gcctgcaggt    540
gctgaacgtg cccgtatgtg atctacatag cggctacact ccggatggtg aattcgatcg    600
ggagaactgt ccctatgagt cctacagaga gatggagttc accgcagctc ttccggtagc    660
acggatggct tatttccatc gacactttt gggggttccc cggccagcac gttcagaaga    720
ggtaagtagt accgtaattg ctgcagccgg agctgcacac aactgcaaga tgctgatgtg    780
atccatagga ctggaagatc tcccccatat ttgcgcctga cttttctgga ctagcacctg    840
cgttggtctt caccgccgaa atggatcctc tgcgggacga aggggaggcc tacgctgcca    900
aattgaaagc tggcggttgt cgagtggaaa tgatgcgtat gcaggagca ccccacacat     960
ttgccatgtt ggatggcatc ttagagagcg gccgtatata taccgagaag gtcatcgaag   1020
cgatgaaacg ggaactaaca gggtaaataa tcaattggtt cggttgaagg atatcgaag    1080
atggagagca gtgttagtgc agagcgacta gaagatggaa atgcggagag acagcaggat   1140
catggtttat ccgacgagaa tctttaccgt atgataccat ttaggccggg cagcgaaggt   1200
gtggcagacg ggtaaccggc gtcctgaaca ttaccgggcc gggagatttc ggcaggcggt   1260
atcggaaaca gttggggtgg attaaatatg cgcggctgct gctgctcttc ttcttccctt   1320
cttttctgcg tggtttgttt gccgtccccc aggttttggg tagaattgga atatcattag   1380
atctgtcgtc ttatattgtt tattttagag agataaagta cgaccaatcc cttgcacaca   1440
tcc                                                                 1443

<210> 4
<211> 1379
<212> DNA
<213> Downstream sequence of fum gene (Unknown)
<400> 4
gcttggagga gtcatctagc gaagactagc ttttgcctag gagatatttg tatactcagg     60
aatactactg tactattctt cttgttcagc ttattgcttg gatagagttc ttcgctgtac    120
ggagtataga attttctcgg gctgatgacg gggctgaccc cggggtgtgc tattttttgga    180
ccaccaaagc ggtcccgccc accgatcgaa tagttcaaga tgcacggata gcaacgactg    240
acggtgtgtt gctgagggcc agtcaagtgg tgttaaattt aggcatacta actagtaacg    300
ttgctgcgcc agtcaggctt ggagggtgat cggcttgacc agtgccagtc ggaaagaacc    360
```

-continued

```
gtatgtagtg gtaagtagta agtagtcagg ggcggatttc caaagtgttt ggtgtttcag    420
gcaaaccgtg ggcccttctc ttactgcttg tttattacct ccgcctggcc ctttcttttc    480
catcaccgac tgaccgactg actcgattga cctgtccttt ttttcccttc atcccttttcc   540 ccctcaaata ctcaccttcg ttggaaatac tctgtctttc gttcaaacac tcactatcac    600
tgaagaaatc cttcattcca gcgtttcaat aattcccatc cgttttcacc actcaattga    660
accccgccac taaccagggg cccttcctcc cttaactaaa ctaccaaaca acctcttcac    720
gaaactcctc aaagccttt tctcctctcc agcaaaaagt tcaagacgga caaaaaacat    780
accaccgcca acatgaccaa cgcctccacc ctcacccaac cccccgccga atccaaggac    840
gacgcccccc tcttccctac gaccctcatc tccccctccg tcgccgccga actgcccgaa    900
ggctacaaga tccgtcccgt ccgtcgctcc gactacagcc gcggctacct ggacgtgttg    960
cgcgtgctga cgaccgtcgg caccatcacc gaggagcagt ggaacaagcg ctacgactgg   1020
atctcgtcgc gcaatgacga gtactacctg cttgttatct gtgacgggga ggatcgtgtc   1080
gtgggcacgg gcagcttgat tgttgagcgc aagttcattc atgagttggg tcttgtgggc   1140
catattgagg acattgccgt cgagaagggc cagcagggga agaggctcgg gctgaggctt   1200
attcaggcgt tggattatgt tgcggcgcag gtgggatgct acaaggtatg tcttctactt   1260
cttattatgg gagtggtggt cgtcatgatg ctaatggtca atgcagagta ttctcgattg   1320
ctccgaggcg aatgagggat tctacctcaa gtgcggcttc aagcgtgctg gattggaga   1379
```

<210> 5
<211> 41
<212> DNA
<213> fum-F-F (Unknown)
<400> 5
gctccgtaac acccagaatt ccccagccaa gtatgccatt g                         41

<210> 6
<211> 41
<212> DNA
<213> fum-F-R (Unknown)
<400> 6
cgaagttatg gatccgagct cggatgtgtg caagggattg g                         41

<210> 7
<211> 42
<212> DNA
<213> fum-R-F (Unknown)
<400> 7
gctatacgaa gttattctag agcttggagg agtcatctag cg                        42

<210> 8
<211> 41
<212> DNA
<213> fum-R-R (Unknown)
<400> 8
tgcctgcagg ggcccactag ttctccaatc cagcacgctt g                         41

<210> 9
<211> 20
<212> DNA
<213> P1 (Unknown)
<400> 9
ccacttcaca acagcatccc                                                 20

<210> 10
<211> 19
<212> DNA
<213> P2 (Unknown)
<400> 10
catcatcacg cgcgttagt                                                  19

<210> 11
<211> 19
<212> DNA
<213> P3 (Unknown)
<400> 11

-continued ctctgagcga ggaggactt                                                    19

<210> 12
<211> 20
<212> DNA
<213> P4 (Unknown)
<400> 12
cagattacct ccagccatcc                                                   20

<210> 13
<211> 20
<212> DNA
<213> P641 (Unknown)
<400> 13
caatatcagt taacgtcgac                                                   20

<210> 14
<211> 20
<212> DNA
<213> P642 (Unknown)
<400> 14
ggaaccagtt aacgtcgaat                                                   20

---

SEQUENCE LISTING

<160> NUMBER OF SEQ ID NOS: 14

<210> SEQ ID NO 1
<211> LENGTH: 2384
<212> TYPE: DNA
<213> ORGANISM: Artificial Sequence
<220> FEATURE:
<223> OTHER INFORMATION: synthesized

<400> SEQUENCE: 1
ttgccgtccc ccaggttttg ggtagaattg gaatatcatt agatctgtcg tcttatattg    60
tttattttag agagataaag tacgaccaat cccttgcaca catcctcgac aggatgtgaa   120
ttgtttccca aaaaatggca ccattggtta gccagccaca cacagtgact aacgcgcgtg   180
atgatgaata gatccagaag ccggtcgtca tgttgacatc tgcccacact tcccgagccg   240
cggtgcgctc gatggcctcc ttgacacatg ctgcatctcg agcttcggct tccccgcag    300 ttgcccgcac tgccgtcgct ttcaccccg cctcgttcag ttgccgtcgt cttctgagct   360
ccaatagccg acctgttcaa cacttccccc gtcttcagac cttgacttcc acctccagca   420
agagagcctt tggcaccacc gtcaagatgg tatgctctat cctttccatt gaatcgcatc   480
tatcatatgg atgacttcgc tatggggaaa gagcccccaac tgcgagacgt tgctaatcgg   540
ttattgtttt agtcttcggc tacccgcatt gagaccgatg ccttcggtga gatcgaggta   600
tgtgctacac tgatgcacac gatgcgtata gaatgcgaat gctgactgct tttcttttct   660
aggtccccgc cgacaagtac tggggtgccc agacccagcg gtaagacccc gatttcaaca   720
atcgctgcca cactgcaaac tggctatgcg accgatacac gaagtgagca gatgctgact   780
ggcgcgacaa tagctccctg gcaacttcg acatcaacca gccccaggac cgcatgcctg   840
agcccgttgt caaggctttc ggtatcctca agggtgctgc tgctgaagtg aacatgaagt   900
tcggccttgg taagccgcta tcgattaaag cagcacagct ccggcgaagt taacaccagg   960
aaattagacc ccaagatcgg cgaggccatc aagcaggctg ccgccgaggt tgcggagggc  1020
aagctgatgg accacttccc cctcgtcgtc tggcagaccg gttccggtac ccagtccaac  1080
atgaactcga acgaggtcat ctccaaccgc gccattgaga tcctgggcgg cgagaagggc  1140
tccaagaagc ccgtccaccc caacgaccac gtcaacatgt ccgcctcctc caatgactcc  1200
ttcccgaccg ctatgcacat tgctgccgtt gtggagctgg agaacaccct cctgccttcc  1260

-continued

```
ctgaggagcc tgcgcgatgc tctccaggtc aaggttgaga agttcgacaa gatcatcaag    1320
atcggtcgta ctcacctgca ggacgccacc cctctcaccc tcggtcagga gttctccggc    1380
tacgtcgctc agctcgaccg caacattgag cgtgtcgaga ctagcatccc ccacctccgc    1440
tacctggctc agggtggtac cgccgtcggt actggtctga acaccttcaa gggcttcgac    1500
gaggctatcg ctgctgaggt caccaagttg accggcaccg agttcaagac tgcccccaac    1560
aagttcgagg ttctggccgc ccacgactcg attgtcgagg cttccggtgc cctgaacacc    1620
ctggcctgct ctctgttcaa gattgcccag gacatccgtt accttggatc cggtccccgc    1680
tgcggtcttg gtgaactggt cctccccgag aacgagcctg gctcttccat catgcccggc    1740
aaggttaacc ccactcagtg cgagtccctt accatggtct gctcccaggt catgggtaac    1800
cacgtcgctg ccactgtcgg cggcatgaac ggtcagttcg agctcaacgt gttcaagccc    1860
ctcatgatcc gcaacctgct gcacagcgtg cgcatcctgg ccgatggcat ggccagcttc    1920
gagaagaacc tggtgcacgg tctggaggcc aacgagcccc gcatcaactc tctcctccac    1980
gagaggtatg tatttcccta aaaaatcgga cctttgtaaa gaagacaact aacggtggtg    2040
tagtctgatg ttggtcacct gcctgaaccc cgtcattggc tacgacatgg cctccaaggt    2100
cgccaagaac gcccacaaga agggcctcac tctgaagcag agtgctatgg agctgaaggc    2160
tctgagcgag gaggactttg acaagtacgt ccgcccggag ctgatgctga gcccaaggga    2220
gaagaaataa atgtatagcg ggacgagaga tgttttggct tagcttggag gagtcatcta    2280
gcgaagacta gcttttgcct aggagatatt tgtatactca ggaatactac tgtactattc    2340
ttcttgttca gcttattgct tggatagagt tcttcgctgt acgg                    2384
```

<210> SEQ ID NO 2
<211> LENGTH: 547
<212> TYPE: PRT
<213> ORGANISM: Artificial Sequence
<220> FEATURE:
<223> OTHER INFORMATION: synthesized

<400> SEQUENCE: 2

```
Met Leu Thr Ser Ala His Thr Ser Arg Ala Ala Val Arg Ser Met Ala
1               5                   10                  15

Ser Leu Thr His Ala Ala Ser Arg Ala Ser Ala Ser Pro Ala Val Ala
            20                  25                  30

Arg Thr Ala Val Ala Phe Thr Pro Ala Ser Phe Ser Cys Arg Arg Leu
        35                  40                  45

Leu Ser Ser Asn Ser Arg Pro Val Gln His Phe Pro Arg Leu Gln Thr
    50                  55                  60

Leu Thr Ser Thr Ser Ser Lys Arg Ala Phe Gly Thr Thr Val Lys Met
65                  70                  75                  80

Ser Ser Ala Thr Arg Ile Glu Thr Asp Ala Phe Gly Glu Ile Glu Val
                85                  90                  95

Pro Ala Asp Lys Tyr Trp Gly Ala Gln Thr Gln Arg Ser Leu Gly Asn
            100                 105                 110

Phe Asp Ile Asn Gln Pro Gln Asp Arg Met Pro Glu Pro Val Val Lys
        115                 120                 125

Ala Phe Gly Ile Leu Lys Gly Ala Ala Ala Glu Val Asn Met Lys Phe
    130                 135                 140

Gly Leu Asp Pro Lys Ile Gly Glu Ala Ile Lys Gln Ala Ala Ala Glu
145                 150                 155                 160
```

Val Ala Glu Gly Lys Leu Met Asp His Phe Pro Leu Val Val Trp Gln
            165                 170                 175
Thr Gly Ser Gly Thr Gln Ser Asn Met Asn Ser Asn Glu Val Ile Ser
        180                 185                 190
Asn Arg Ala Ile Glu Ile Leu Gly Gly Glu Lys Gly Ser Lys Lys Pro
    195                 200                 205
Val His Pro Asn Asp His Val Asn Met Ser Ala Ser Ser Asn Asp Ser
210                 215                 220
Phe Pro Thr Ala Met His Ile Ala Ala Val Glu Leu Glu Asn Thr
225                 230                 235                 240
Leu Leu Pro Ser Leu Arg Ser Leu Arg Asp Ala Leu Gln Val Lys Val
            245                 250                 255
Glu Lys Phe Asp Lys Ile Ile Lys Ile Gly Arg Thr His Leu Gln Asp
        260                 265                 270
Ala Thr Pro Leu Thr Leu Gly Gln Glu Phe Ser Gly Tyr Val Ala Gln
    275                 280                 285
Leu Asp Arg Asn Ile Glu Arg Val Glu Thr Ser Ile Pro His Leu Arg
290                 295                 300
Tyr Leu Ala Gln Gly Gly Thr Ala Val Gly Thr Gly Leu Asn Thr Phe
305                 310                 315                 320
Lys Gly Phe Asp Glu Ala Ile Ala Ala Glu Val Thr Lys Leu Thr Gly
            325                 330                 335
Thr Glu Phe Lys Thr Ala Pro Asn Lys Phe Glu Val Leu Ala Ala His
        340                 345                 350
Asp Ser Ile Val Glu Ala Ser Gly Ala Leu Asn Thr Leu Ala Cys Ser
    355                 360                 365
Leu Phe Lys Ile Ala Gln Asp Ile Arg Tyr Leu Gly Ser Gly Pro Arg
370                 375                 380
Cys Gly Leu Gly Glu Leu Val Leu Pro Glu Asn Glu Pro Gly Ser Ser
385                 390                 395                 400
Ile Met Pro Gly Lys Val Asn Pro Thr Gln Cys Glu Ser Leu Thr Met
            405                 410                 415
Val Cys Ser Gln Val Met Gly Asn His Val Ala Ala Thr Val Gly Gly
        420                 425                 430
Met Asn Gly Gln Phe Glu Leu Asn Val Phe Lys Pro Leu Met Ile Arg
    435                 440                 445
Asn Leu Leu His Ser Val Arg Ile Leu Ala Asp Gly Met Ala Ser Phe
450                 455                 460
Glu Lys Asn Leu Val His Gly Leu Glu Ala Asn Glu Pro Arg Ile Asn
465                 470                 475                 480
Ser Leu Leu His Glu Ser Leu Met Leu Val Thr Cys Leu Asn Pro Val
            485                 490                 495
Ile Gly Tyr Asp Met Ala Ser Lys Val Ala Lys Asn Ala His Lys Lys
        500                 505                 510
Gly Leu Thr Leu Lys Gln Ser Ala Met Glu Leu Lys Ala Leu Ser Glu
    515                 520                 525
Glu Asp Phe Asp Lys Tyr Val Arg Pro Glu Leu Met Leu Ser Pro Lys
530                 535                 540
Glu Lys Lys
545

<210> SEQ ID NO 3
<211> LENGTH: 1443
<212> TYPE: DNA

<213> ORGANISM: Artificial Sequence
<220> FEATURE:
<223> OTHER INFORMATION: synthesized

<400> SEQUENCE: 3

```
cccagccaag tatgccattg cctacggccg tgctcaaggt cctgatgtct tccgcatcac    60
ggagcagaaa tgtcccgtgc aaggggggcga gataaccatc cgtatcttcg agcctgcccc   120
gaaagcggat gagcatggca aggccaaaaa gagggctgcg tttgtcaact tccatggggg   180
aggctgggtg ttcggcgatc tctcagttga tcacgatttc tgcaagacac tcgtcgatgg   240
cctggacggg cacttggtcg cgtttgatgt cgactaccgg ctagctcctg agcacaagta   300
cccgatcccc gttgacgact gctggaccgc tttcaattgg gtcagctaca actccctgtc   360
tacatcgacc ggtatggtca atactaactg acatcccgtg cagatccgct cccagaaagc   420
agaggagttc aacgttgacc cgaatcgaat agctgttgga ggttgttcgg ccggaggcca   480
cctgtcagcc gtggtcgctc atctctgccg taatggcggc attccgttgc gcctgcaggt   540
gctgaacgtg cccgtatgtg atctacatag cggctacact ccggatggtg aattcgatcg   600
ggagaactgt ccctatgagt cctacagaga gatggagttc accgcagctc ttccggtagc   660
acggatggct tatttccatc gacacttttt gggggttccc cggccagcac gttcagaaga   720
ggtaagtagt accgtaattg ctgcagccgg agctgcacac aactgcaaga tgctgatgtg   780
atccatagga ctgaagatc tcccccatat ttgcgcctga cttttctgga ctagcacctg   840
cgttggtctt caccgccgaa atggatcctc tgcgggacga aggggaggcc tacgctgcca   900
aattgaaagc tggcggttgt cgagtggaaa tgatgcgtat ggcaggagca ccccacacat   960
ttgccatgtt ggatggcatc ttagagagcg gccgtatata taccgagaag gtcatcgaag  1020
cgatgaaacg ggaactaaca gggtaaataa tcaattggtt cggttgaagg gatatcgaag  1080
atggagagca gtgttagtgc agagcgacta gaagatggaa atgcggagag acagcaggat  1140
catggtttat ccgacgagaa tctttaccgt atgataccat ttaggccggg cagcgaaggt  1200
gtggcagacg ggtaaccggc gtcctgaaca ttaccgggcc gggagatttc ggcaggcggt  1260
atcggaaaca gttggggtgg attaaatatg cgcggctgct gctgctcttc ttcttcccctt  1320
ctttctgcg tggtttgttt gccgtccccc aggttttggg tagaattgga atatcattag  1380
atctgtcgtc ttatattgtt tattttagag agataaagta cgaccaatcc cttgcacaca  1440
tcc                                                                 1443
```

<210> SEQ ID NO 4
<211> LENGTH: 1379
<212> TYPE: DNA
<213> ORGANISM: Artificial Sequence
<220> FEATURE:
<223> OTHER INFORMATION: synthesized

<400> SEQUENCE: 4

```
gcttggagga gtcatctagc gaagactagc ttttgcctag gagatatttg tatactcagg    60
aatactactg tactattctt cttgttcagc ttattgcttg gatagagttc ttcgctgtac   120
ggagtataga attttctcgg gctgatgacg gggctgaccc cggggtgtgc tattttttgga  180
ccaccaaagc ggtcccgccc accgatcgaa tagttcaaga tgcacggata gcaacgactg   240
acggtgtgtt gctgagggcc agtcaagtgg tgttaaattt aggcatacta actagtaacg   300
ttgctgcgcc agtcaggctt ggagggtgat cggcttgacc agtgccagtc ggaaagaacc   360
gtatgtagtg gtaagtagta agtagtcagg ggcggatttc caaagtgttt ggtgtttcag   420
```

```
gcaaaccgtg ggcccttctc ttactgcttg tttattacct ccgcctggcc ctttcttttc    480
catcaccgac tgaccgactg actcgattga cctgtccttt ttttcccttc atccctttcc    540
ccctcaaata ctcaccttcg ttggaaatac tctgtctttc gttcaaacac tcactatcac    600
tgaagaaatc cttcattcca gcgtttcaat aattcccatc cgttttcacc actcaattga    660
accccgccac taaccagggg cccttcctcc cttaactaaa ctaccaaaca acctcttcac    720
gaaactcctc aaagccttt tctcctctcc agcaaaaagt tcaagacgga caaaaaacat    780
accaccgcca acatgaccaa cgcctccacc ctcacccaac ccccgccga tccaaggac     840 gacgccccc tcttccctac gaccctcatc tccccctccg tcgccgccga actgcccgaa    900
ggctacaaga tccgtcccgt ccgtcgctcc gactacagcc gcggctacct ggacgtgttg    960
cgcgtgctga cgaccgtcgg caccatcacc gaggagcagt ggaacaagcg ctacgactgg   1020
atctcgtcgc gcaatgacga gtactacctg cttgttatct gtgacgggga ggatcgtgtc   1080
gtgggcacgg gcagcttgat tgttgagcgc aagttcattc atgagttggg tcttgtgggc   1140
catattgagg acattgccgt cgagaagggc cagcagggga agaggctcgg gctgaggctt   1200
attcaggcgt tggattatgt tgcggcgcag gtgggatgct acaaggtatg tcttctactt   1260
cttattatgg gagtggtggt cgtcatgatg ctaatggtca atgcagagta ttctcgattg   1320
ctccgaggcg aatgagggat tctacctcaa gtgcggcttc aagcgtgctg gattggaga    1379

<210> SEQ ID NO 5
<211> LENGTH: 41
<212> TYPE: DNA
<213> ORGANISM: Artificial Sequence
<220> FEATURE:
<223> OTHER INFORMATION: synthesized

<400> SEQUENCE: 5
gctccgtaac acccagaatt ccccagccaa gtatgccatt g                         41

<210> SEQ ID NO 6
<211> LENGTH: 41
<212> TYPE: DNA
<213> ORGANISM: Artificial Sequence
<220> FEATURE:
<223> OTHER INFORMATION: synthesized

<400> SEQUENCE: 6
cgaagttatg gatccgagct cggatgtgtg caagggattg g                         41

<210> SEQ ID NO 7
<211> LENGTH: 42
<212> TYPE: DNA
<213> ORGANISM: Artificial Sequence
<220> FEATURE:
<223> OTHER INFORMATION: synthesized

<400> SEQUENCE: 7
gctatacgaa gttattctag agcttggagg agtcatctag cg                        42

<210> SEQ ID NO 8
<211> LENGTH: 41
<212> TYPE: DNA
<213> ORGANISM: Artificial Sequence
<220> FEATURE:
<223> OTHER INFORMATION: synthesized

<400> SEQUENCE: 8
```

```
tgcctgcagg ggcccactag ttctccaatc cagcacgctt g                             41
```

<210> SEQ ID NO 9
<211> LENGTH: 20
<212> TYPE: DNA
<213> ORGANISM: Artificial Sequence
<220> FEATURE:
<223> OTHER INFORMATION: synthesized

<400> SEQUENCE: 9

```
ccacttcaca acagcatccc                                                     20
```

<210> SEQ ID NO 10
<211> LENGTH: 19
<212> TYPE: DNA
<213> ORGANISM: Artificial Sequence
<220> FEATURE:
<223> OTHER INFORMATION: synthesized

<400> SEQUENCE: 10

```
catcatcacg cgcgttagt                                                      19
```

<210> SEQ ID NO 11
<211> LENGTH: 19
<212> TYPE: DNA
<213> ORGANISM: Artificial Sequence
<220> FEATURE:
<223> OTHER INFORMATION: synthesized

<400> SEQUENCE: 11

```
ctctgagcga ggaggactt                                                      19
```

<210> SEQ ID NO 12
<211> LENGTH: 20
<212> TYPE: DNA
<213> ORGANISM: Artificial Sequence
<220> FEATURE:
<223> OTHER INFORMATION: synthesized

<400> SEQUENCE: 12

```
cagattacct ccagccatcc                                                     20
```

<210> SEQ ID NO 13
<211> LENGTH: 20
<212> TYPE: DNA
<213> ORGANISM: Artificial Sequence
<220> FEATURE:
<223> OTHER INFORMATION: synthesized

<400> SEQUENCE: 13

```
caatatcagt taacgtcgac                                                     20
```

<210> SEQ ID NO 14
<211> LENGTH: 20
<212> TYPE: DNA
<213> ORGANISM: Artificial Sequence
<220> FEATURE:
<223> OTHER INFORMATION: synthesized

<400> SEQUENCE: 14

```
ggaaccagtt aacgtcgaat                                                     20
```

We claim:

1. A method of constructing an *Aspergillus niger* engineered strain for reducing byproduct fumaric acid in a fermentation process of L-malic acid, wherein a fumarate hydratase gene fum is knocked out from the *Aspergillus niger* engineered strain;

the amino acid sequence encoded by the fumarate hydratase gene fum is SEQ NO:2;

the gene sequence of the fumarate hydratase gene fum is NCBI-locus_tagANI_1_952104;

the method comprises:

(1) respectively amplifying upstream and downstream sequence fragments of a gene fum through PCR reaction with a wild type *Aspergillus niger* ATCC1015 genome as a template, and recovering PCR products to respectively obtain target fragments; and cloning the upstream and downstream sequence fragments of the gene fum onto a vector pLH594, so as to construct a fumarate hydratase gene fum knockout vector pLH804;

wherein the upstream sequence of the gene fum is SEQ NO:3, and the downstream sequence of the gene fum is SEQ NO: 4;

(2) transferring the vector pLH804 into an *Aspergillus niger* malic acid high-yield strain S1149, and conducting transformant screening and hygromycin resistance gene recombination to obtain an *Aspergillus niger* fumarate hydratase gene fum knockout strain M1, wherein the *Aspergillus niger* engineered strain is obtained by knocking out only the gene sequence of the fumarate hydratase gene fum.

* * * * *